United States Patent
Sallam et al.

(10) Patent No.: US 11,020,337 B2
(45) Date of Patent: Jun. 1, 2021

(54) ASPARTYL-DIPEPTIDES FOR SKIN CARE AND COSMETIC USE

(71) Applicant: Cysal GmbH, Muenster (DE)

(72) Inventors: Ahmed Sallam, Muenster (DE);
Martin Krehenbrink, Muenster (DE);
Dimitar Kalkandzhiev, Muenster (DE)

(73) Assignee: Cysal GmbH, Muenster (DE)

( * ) Notice: Subject to any disclaimer, the term of this patent is extended or adjusted under 35 U.S.C. 154(b) by 0 days.

(21) Appl. No.: 16/087,504

(22) PCT Filed: Mar. 24, 2017

(86) PCT No.: PCT/EP2017/057127
§ 371 (c)(1),
(2) Date: Sep. 21, 2018

(87) PCT Pub. No.: WO2017/162879
PCT Pub. Date: Sep. 28, 2017

(65) Prior Publication Data
US 2019/0117548 A1    Apr. 25, 2019

(30) Foreign Application Priority Data

Mar. 24, 2016   (EP) .................................... 16162239

(51) Int. Cl.
*A61K 8/64* (2006.01)
*A61Q 5/00* (2006.01)
(Continued)

(52) U.S. Cl.
CPC .............. *A61K 8/64* (2013.01); *A61K 8/0212* (2013.01); *A61K 8/046* (2013.01); *A61K 8/44* (2013.01);
(Continued)

(58) Field of Classification Search
CPC . A61Q 19/08; A61Q 5/00; A61Q 5/12; A61Q 7/00; A61K 8/44; A61K 8/0212; A61K 8/64
See application file for complete search history.

(56) References Cited

U.S. PATENT DOCUMENTS 5,478,560 A    12/1995 Tominaga et al.
2009/0068255 A1*  3/2009 Yu .................... A61K 8/0212
                                                424/450

FOREIGN PATENT DOCUMENTS

CN    102066559 A     5/2011
EP    2 133 419 A1   12/2009
(Continued)

OTHER PUBLICATIONS

International Search Report and Written Opinion of the International Searching Authority dated May 16, 2017 (twelve pages).
(Continued)

*Primary Examiner* — Jianfeng Song
(74) *Attorney, Agent, or Firm* — Kilpatrick Townsend & Stockton LLP

(57) ABSTRACT

The invention provides a cosmetic composition for skin and/or hair care comprising one or more β-aspartyl dipeptides, or oligomers thereof, or salts thereof, wherein each of said β-aspartyl dipeptides comprises a β-L-aspartyl moiety as the first amino acid residue. The invention further relates to a method for human skin and/or hair care, including anti-aging and/or anti-hair loss utilizing this composition.

14 Claims, 6 Drawing Sheets

Figure 1:
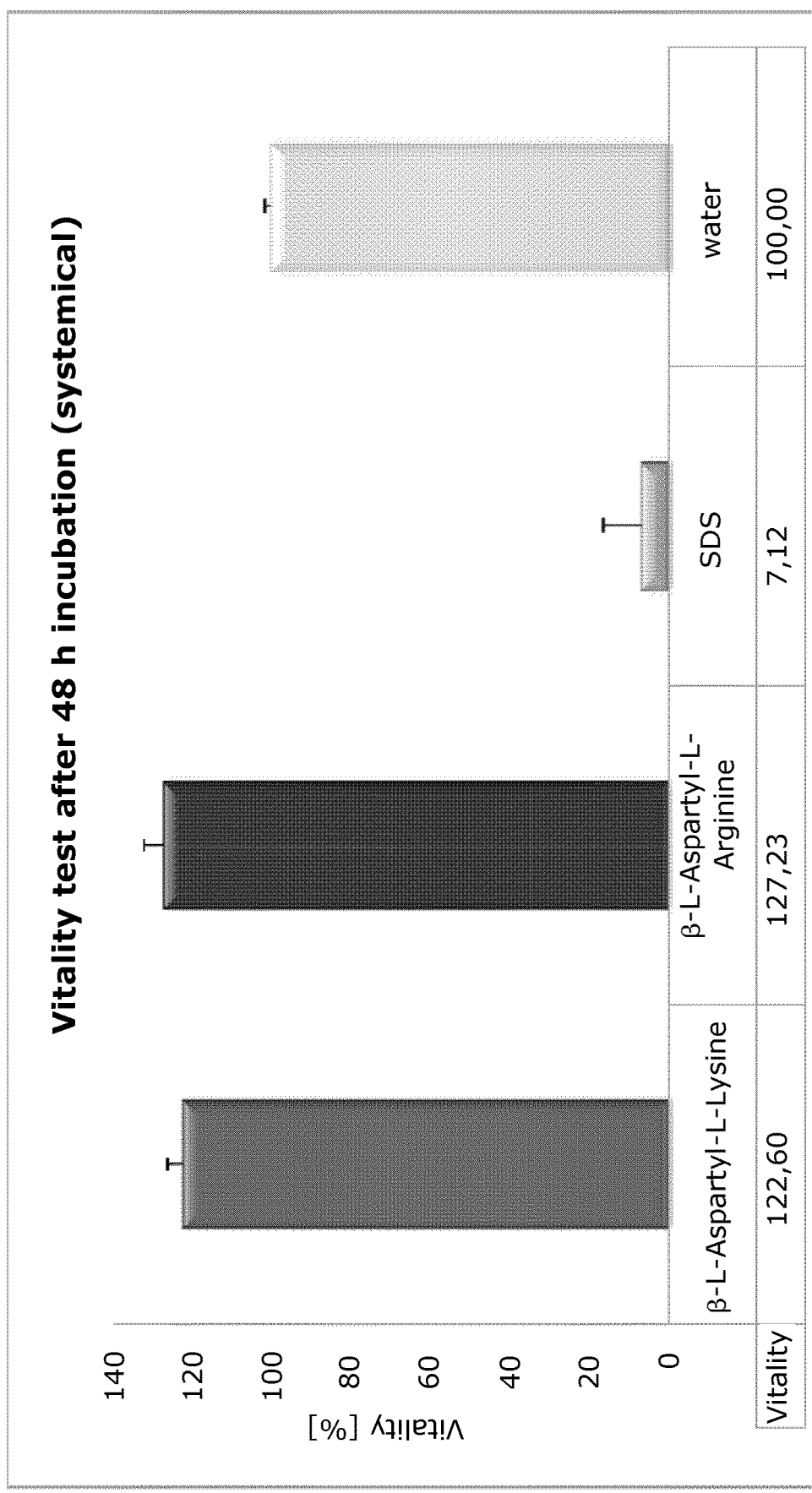

(51) Int. Cl.
*A61Q 19/00* (2006.01)
*A61Q 19/08* (2006.01)
*A61Q 5/12* (2006.01)
*A61Q 7/00* (2006.01)
*A61K 8/02* (2006.01)
*A61K 8/04* (2006.01)
*A61K 8/44* (2006.01)

(52) U.S. Cl.
CPC ................ *A61Q 5/00* (2013.01); *A61Q 5/12* (2013.01); *A61Q 7/00* (2013.01); *A61Q 19/007* (2013.01); *A61Q 19/08* (2013.01)

(56) References Cited

FOREIGN PATENT DOCUMENTS

| EP | 21333419 | * | 12/2009 |
| KR | 2010092150 | * | 8/2010 |
| WO | 2006/116731 A2 | | 11/2006 |
| WO | 2009/150252 A2 | | 12/2009 |
| WO | 2011/126163 A1 | | 10/2011 |

OTHER PUBLICATIONS

International Preliminary Report on Patentability dated Oct. 4, 2018 (six pages) from corresponding International Application No. PCT/EP2017/057127.

* cited by examiner

ASPARTYL-DIPEPTIDES FOR SKIN CARE AND COSMETIC USE

This application is a U.S. National Phase Application of PCT/EP2017/057127, filed Mar. 24, 2017, which claims priority to European Patent Application No. 16162239.4, filed Mar. 24, 2016, the entireties of which are incorporated by reference herein.

The invention provides a cosmetic composition comprising one or more β-aspartyl dipeptides, or oligomers thereof, or salts thereof, wherein each of said β-aspartyl dipeptides comprises a β-L-aspartyl moiety as the first amino acid residue. The invention further relates to a method for skin care and/or hair care utilizing this composition.

BACKGROUND OF THE INVENTION

In general, amino acids are widely used in cosmetic products. Among these, aspartic acid, arginine and lysine, as well as salts/mixtures thereof, are considered skin nourishing and/or hair conditioning, for example by the accredited Internet portal "Cosmetic Analysis", an initiative of the German "Institution for Advancement of Skin Health", based on an evaluation of around 8000 components by independent sources. Also the list "Cosmetics-Ingredients-Functions" of the German "Industry Association for Personal Hygiene and Laundry Detergents" (IKW) classifies these amino acids and their salts as "skin caring" and "hair conditioning". Such amino acid salts/mixtures were integrated, for example, in some high quality cosmetics of the Japanese company Shiseido. Dermatological tests with arginine and aspartate described this combination as protective against skin drying and as skin regenerative (see Shiseido's patents EP-B-0506956 and U.S. Pat. No. 5,478,560). However the utility of these mixtures/salts of the amino acids in cosmetic applications is limited by their moderate uptake by skin cells. Also the amino acid arginine alone is known to provide similar effects to skin and to be helpful against hair loss as claimed by the German company Henkel for some of their widely known products. Furthermore, WO2011/126163 discloses skin-whitening compositions containing dipeptides.

SHORT DESCRIPTION OF THE INVENTION

It was now found that β-L-aspartyl dipeptides, notably those known from WO2009150252 do possess highly effective skin and hair caring properties and represent thereby a new form for applying their constitutive amino acids in the field of cosmetics. Said dipeptides are further not bound to the uptake limitation known for free amino acids due to the separate and specialized tri-/dipeptide transports, which do not accept free amino acids or molecules larger than tripeptides (Daniel et al. Physiology 21:93-102 (2006)). The invention thus provides:

(1) a dermatological and/or hair care composition comprising one or more β-dipeptides, or oligomers thereof, or salts thereof, wherein each of the β-dipeptides comprises β-L-aspartyl as a first amino acid residue;

(2) a cosmetic method comprising topically applying the composition as defined in (1) on human or animal skin and/or hair; and (3) the use of the composition as defined in (1) above for vitalizing, conditioning or in an anti-aging treatment of the human or animal skin and/or hair.

SHORT DESCRIPTION OF THE FIGURES

FIG. 1: Summarizes illustration of MU-Vitality-Assay results after 48 h of systematical incubation.

Figure 2:
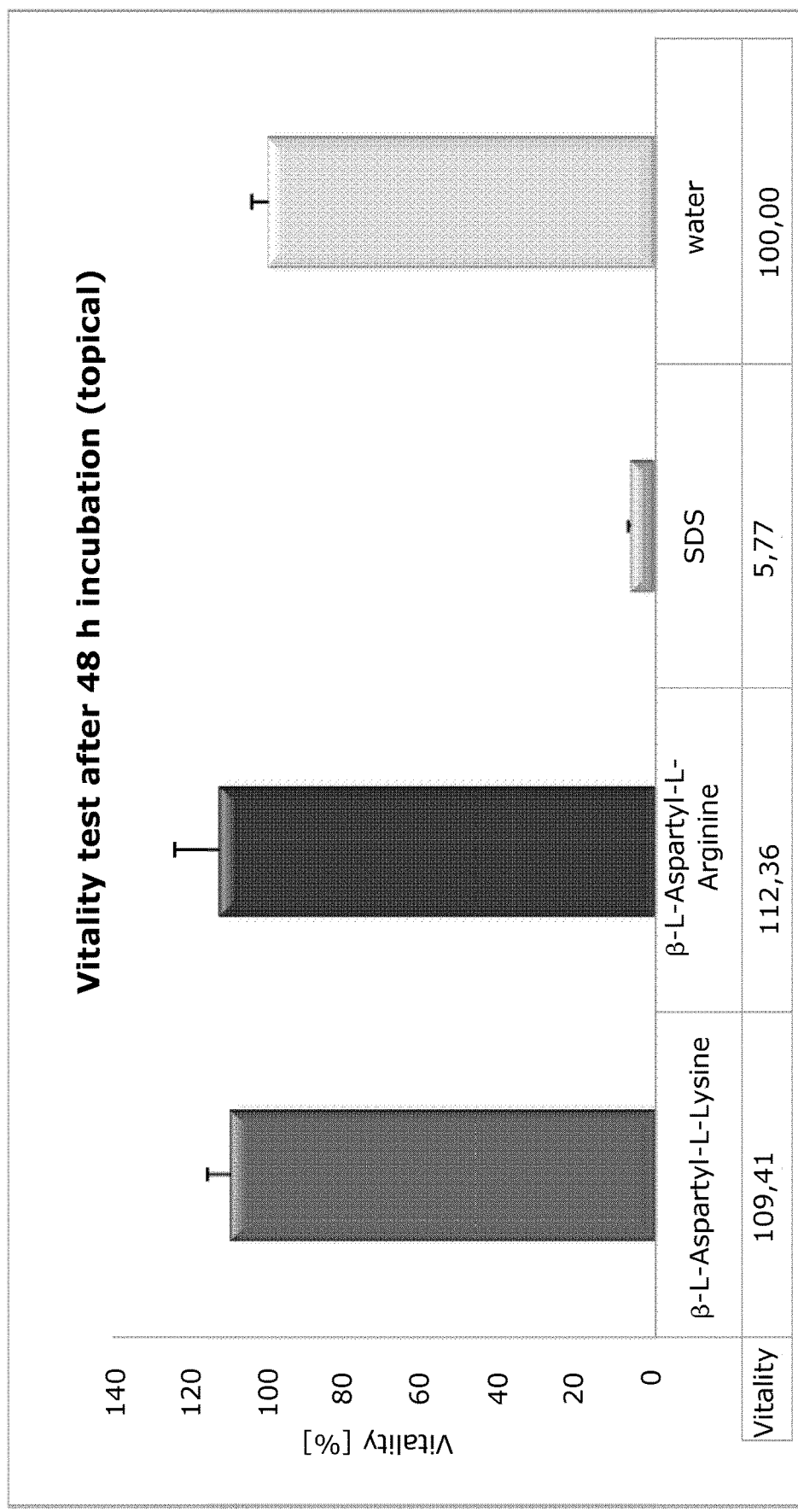

FIG. 2: Summarizes illustration of MU-Vitality-Assay results after 48 h of topical application.

Figure 3:
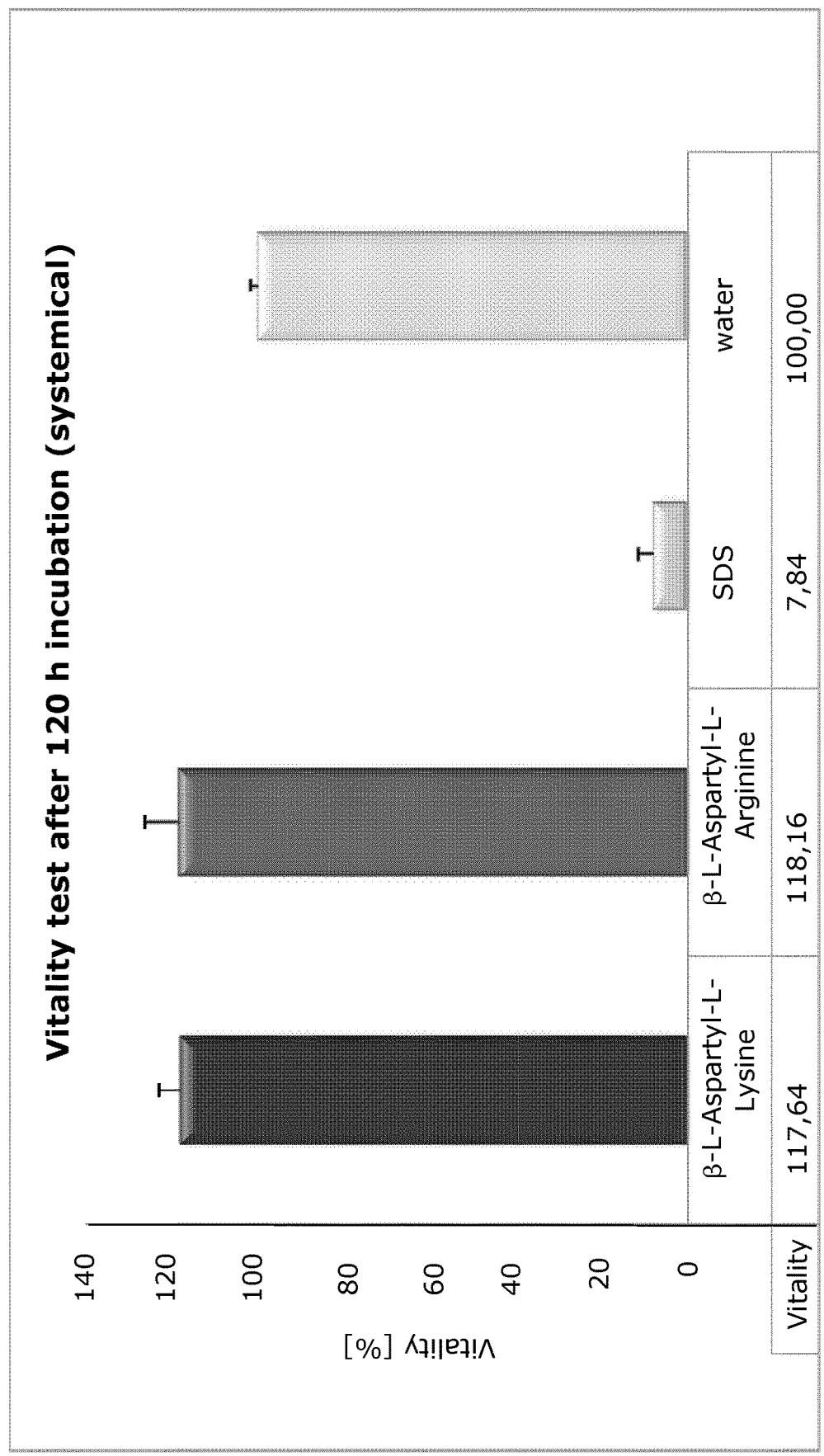

FIG. 3: Summarizes illustration of MU-Assay results after 120 h systematical incubation.

Figure 4:
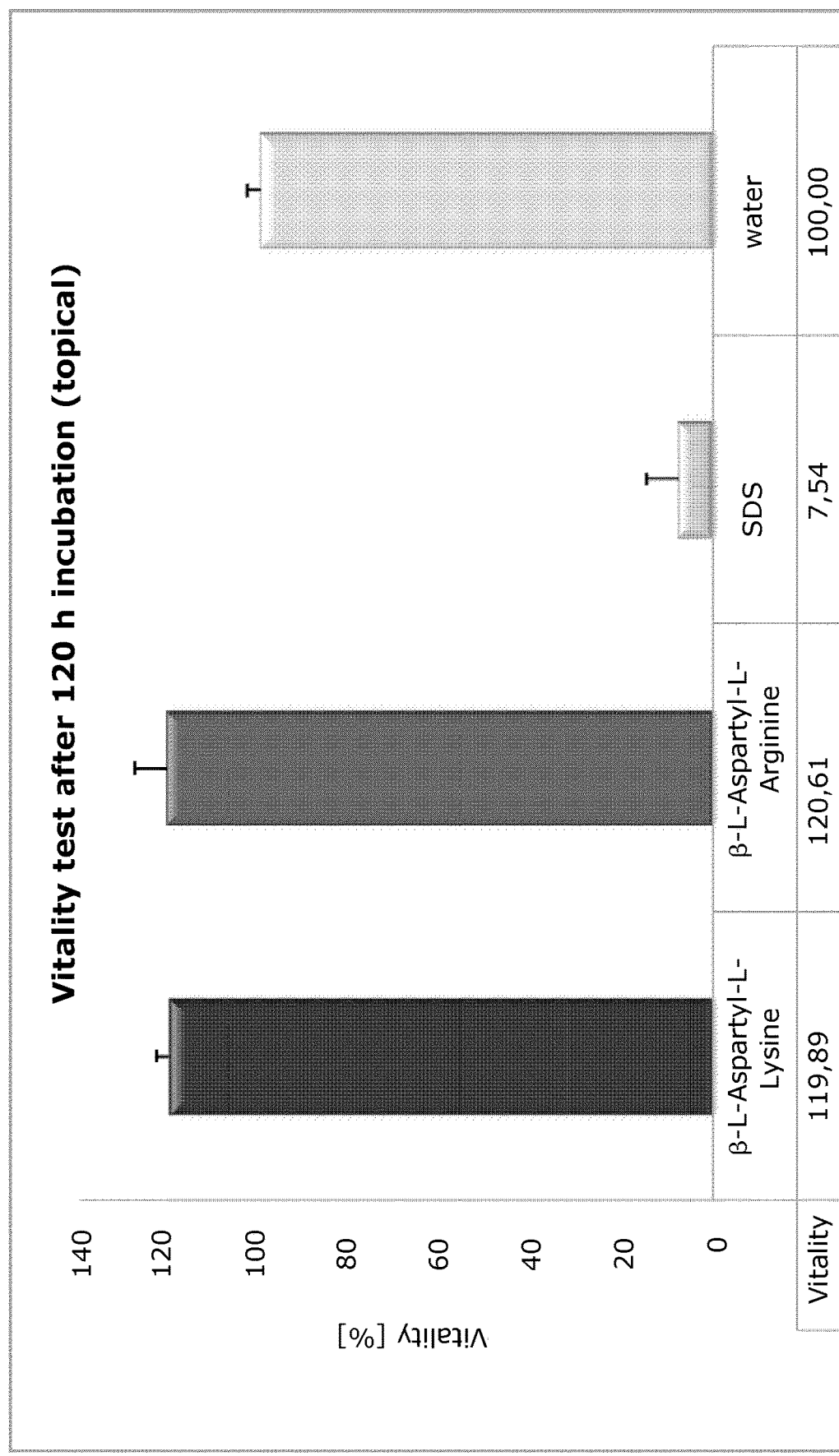

FIG. 4: Summarizes illustration of MU-Assay results after 120 h of topical application.

Figure 5:
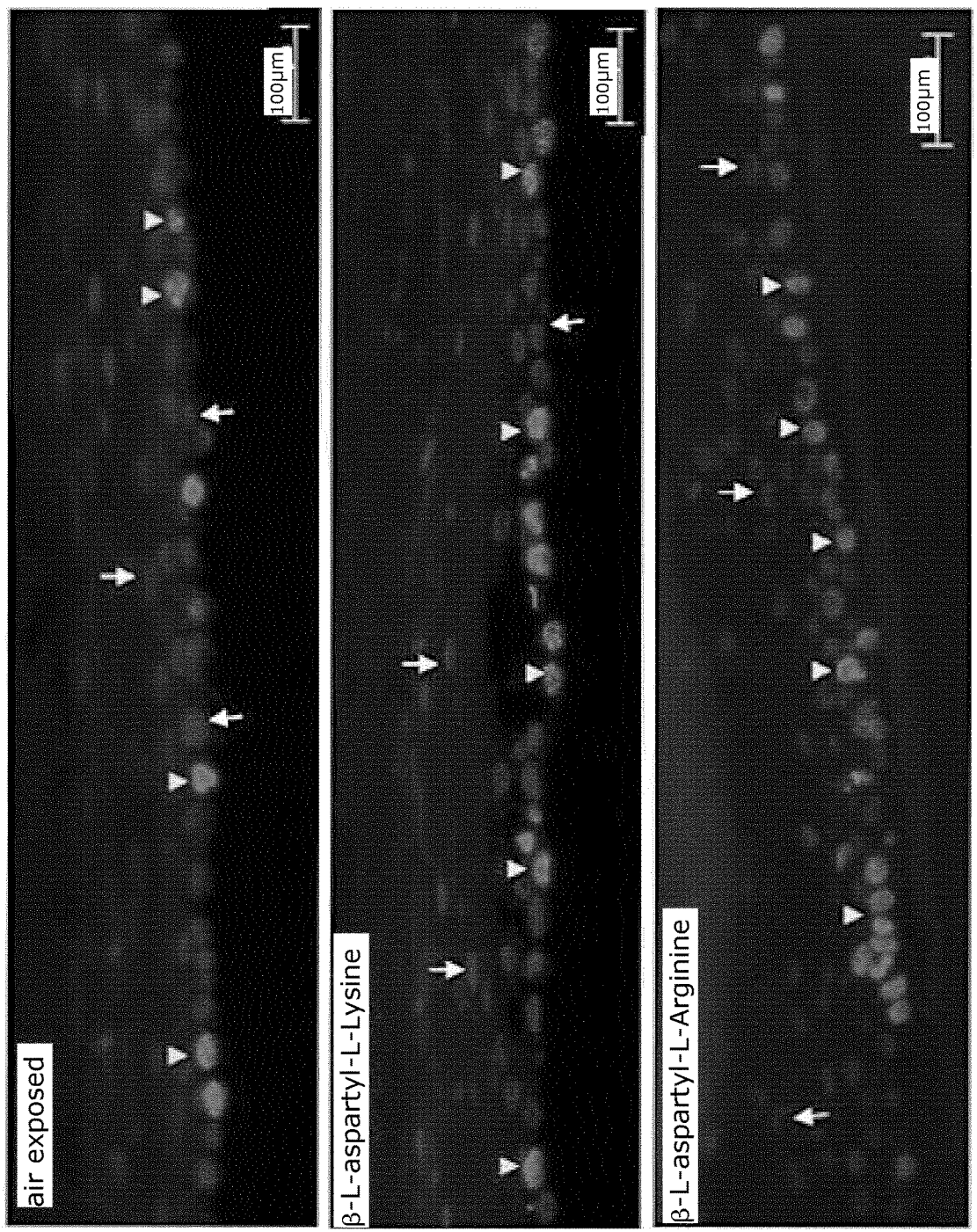

FIG. 5: Exemplarily illustration of proliferating basal keratinocytes after 3 days of exposure. Images (blue and red fluorescence) were taken solely and subsequently merged. Blue fluorescing nuclei (dark dots) were stained with DAPI. Red fluorescence (bright dots) represents proliferative nuclei in the S-Phase of mitosis (Click-iT®-Edu staining). Arrow heads: proliferating cells, arrows: DAPI stained nuclei, not proliferative.

Figure 6:
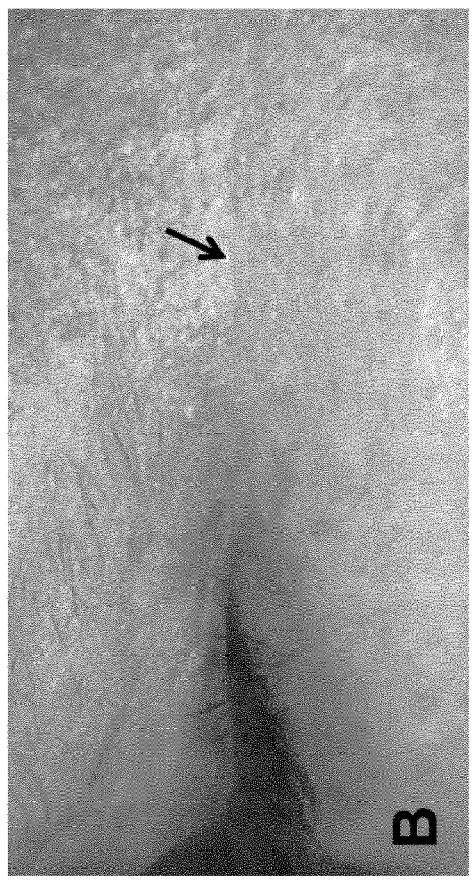
Figure 6:
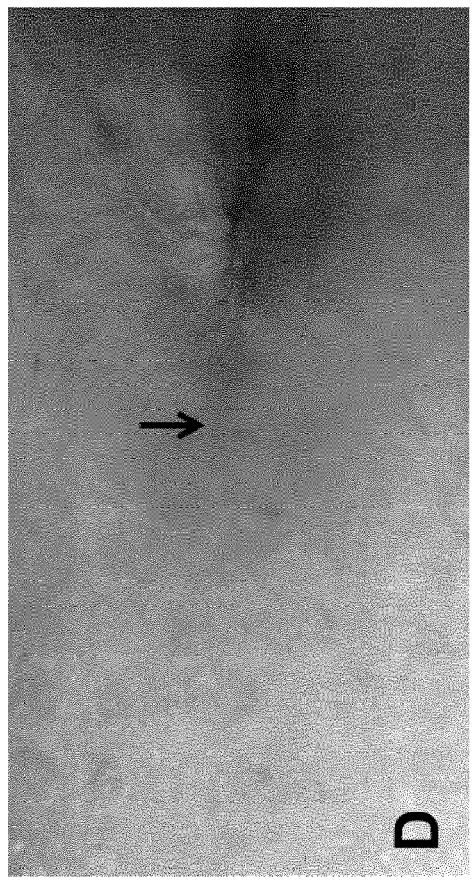
Figure 6:
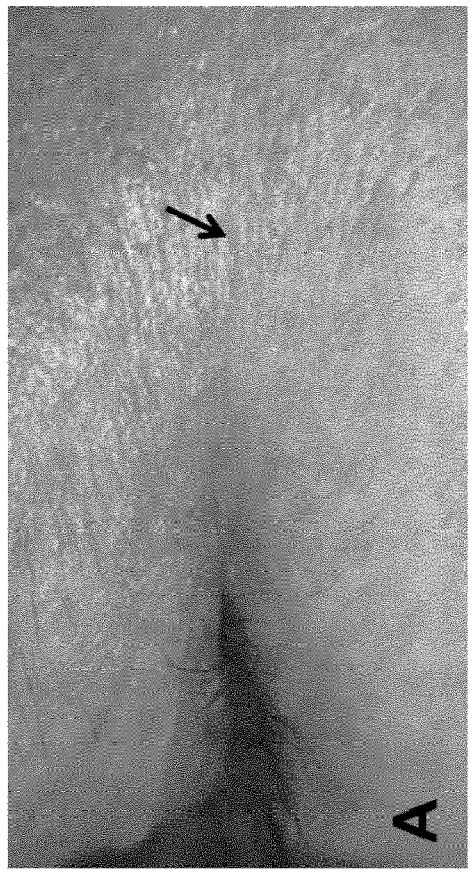
Figure 6:
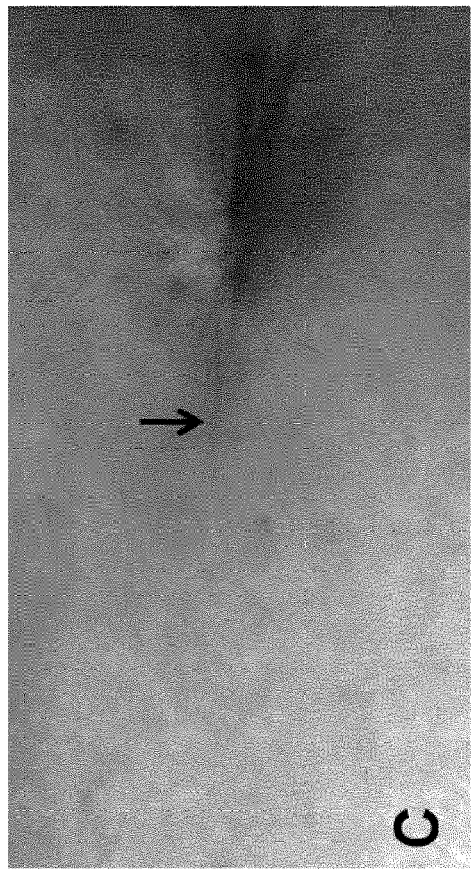

FIG. 6: Images of the crow's feet area (left eye) were taken before (A) and after 4 weeks application of β-L-aspartyl-L-arginine (B); images of the crow's feet area (right eye) were taken before (C) and after 4 weeks application of β-L-aspartyl-L-lysine (D). Arrow: wrinkle that was chosen for optical 3D-measurement of the skin surface with the PRIMOS system.

DETAILED DESCRIPTION OF THE INVENTION

The β-dipeptides or β-dipeptide oligomers of the compositions of aspect (1) of the present invention are derived from cyanophycin, (also abbreviated CGP, Cyanophycin Granule Peptide) or cyanophycin-like polymer by selective hydrolysis.

In nature, and in addition to several heterotrophic bacteria, most cyanobacterial species (blue-green algae) accumulate the polypeptide CGP as a reserve material for carbon and nitrogen. CGP is accumulated in the early stationary growth phase of bacteria and is mostly composed of two amino acids, namely aspartic acid and arginine. One or more amino acids, which are structurally similar to arginine such as lysine, ornithine, glutamate, citrulline, and canavanine, may partially replace the arginine residue of CGP depending on the environmental/cultivation conditions. Compared to chemically-synthesized dipeptides, CGP-dipeptides are natural and stereospecific (structurally homogeneous) substances that are produced from biomass in a biotechnological and environmentally-friendly way. The production of CGP dipeptides furthermore requires much less technological expense and effort, very little time, and significantly less financial effort. As the production process employs neither protecting groups nor harmful or environmentally unsafe solvents, the biocompatibility of these dipeptides is always ensured (Sallam et al. 2009. AEM 75:29-38).

Such CGP β-dipeptide compositions that are obtainable by the degradation/hydrolysis may be composed of a single type of β-dipeptides, or of a mixture of different β-dipeptides, or of a single type of β-dipeptide oligomers, or of a mixture of different β-dipeptide oligomers, or of mixtures of such β-dipeptides and β-dipeptide oligomers. It is however preferred that the β-dipeptides comprise amino acid residues selected from aspartate, arginine, lysine, and other amino acid residues present in CGP or CGP-like polymers. Particularly preferred is that the β-dipeptides are selected from β-L-aspartyl-L-arginine and β-L-aspartyl-L-lysine. A suitable CGPase for the CGP degradation is a CGPase from *P. alcaligenes*, particularly preferred from *P. alcaligenes* strain DIP1. Said CGPase (i) has a molecular weight of 45 kDa, an optimum temperature of 50° C., and an optimum pH range of 7-8.5 and degrades CGP into β-Asp-Arg; and/or (ii) is the *P. alcaligenes* DIP1 CGPase CphE$_{al}$ having been deposited with the DSMZ as DSM 21533, or is a mutant, derivative or fragment thereof capable of cleavage of CGP or CGP-like polymers into dipeptides.

The mutants, derivatives or fragments of the aforementioned native CGPase include fragments (having at least 50 consecutive amino acid residues of the native sequence, preferably N- and/or C-terminal truncation products, wherein up to 50 terminal amino acid residues are removed), derivatives (notably fusion products with functional proteins and peptides such as secretion peptides, leader sequences etc., and reaction products with chemical moieties such as PEG, alcohols, amines etc.) and mutants (notably addition, substitution, inversion and deletion mutants, having at least 80%, preferably at least 90%, most preferably at least 95% sequence identity with the native enzyme on the amino acid basis or wherein 1 to 20, preferably 1 to 10, consecutive or separated amino acid residues are added, substituted, inverted and/or deleted; for substitution mutants conservative substitution is particularly preferred), provided, however, that said modified CGPases have the enzymatic activity of the native CGPase.

The degradation process may be preceded by a step that provides the CGP or CGP-like polymer preparation, namely by culturing a prokaryotic or eukaryotic cell line. The producing cell line may be any cell line capable of producing the CGP or CGP-like polymer. It is preferred that the producing cell line is selected from Escherichia coli, Ralstonia eutropha, Acinetobacter baylyi, Corynebacterium glutamicum, Pseudomonas putida, yeast strains, and plant biomass. Particularly preferred producing cell lines are Ralstonia eutropha H16-PHB$^-$4-Δeda (pBBR1MCS-2::cphA$_{6308}$/edaH16) and E. coli DH1 (pMa/c5-914::cphA$_{PCC6803}$).

The above process may further comprise the steps of isolating, purifying and/or chemically modifying the CGP product obtained by cultivating the producing cell line. Such isolation, purification, chemical modification and separation may be effected by methods well established in the art.

It is however preferred that the CGP product obtained by cultivating the producing cell line is directly, i.e. without isolation or purification, subjected to degradation with the CGPase.

Alternatively, the degradation product may be purified and/or chemically modified. Again, such purification, separation, or chemical modification may be effected by methods well established in the art.

In the composition of aspect (1) each of the one or more β-dipeptides comprises β-L-aspartyl as a first amino acid residue, which is covalently bound to a second amino acid residue. The second amino acid residue may be selected from arginine, lysine, ornithine, glutamate, citrulline, and canavanine. Preferably the second amino acid residue is arginine or lysine. Further, the second amino acid residue may be of L- or D-configuration. Thus, the dipeptides may have the formula I

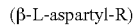
(β-L-aspartyl-R)

and the dipeptide oligomers may have the formula II

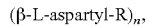
(β-L-aspartyl-R)$_n$, wherein R is independently selected from the amino acid residues defined herein-before and n is an integer of 2 to 150, preferably 2 to 30, most preferably 2 to 10. The dermatologic and/or hair care composition of aspect (1) can further comprise two or more dipeptides as described above that are covalently bound together, and wherein the second amino acid residue of each dipeptide is independently selected, preferably selected from arginine, lysine, ornithine, glutamate, citrulline, and canavanine. Most preferably the second amino acid residue is arginine or lysine. In another embodiment, one or more of the β-dipeptides are chemically modified. Such chemical modification includes phosphorylation, farnesylation, ubiquitination, glycosylation, acetylation, formylation, amidation, sumoylation, biotinylation, N-acylation, esterification, and cyclization. In a preferred embodiment, the composition of aspect (1) comprises from 0.00001 to 50 wt. % of β-dipeptides or oligomers thereof, more preferably from 0.0001 to 10 wt. % and most preferably from 0.01 to 5 wt. %. The composition of aspect (1) may further comprise one or more free amino acids or salts thereof. These free amino acids are preferably selected from arginine, lysine, cysteine, glycin, praline and methionine. The content of free amino acids or salts thereof in the composition is preferably from 0.001 to 10 wt. %.

Oligomers of the β-dipeptides include homomeric (i.e. composed of one β-dipeptide) and heteromeric (i.e. composed of two or more different β-dipeptides) structures, in which the β-dipeptide units are covalently attached to each other.

The β-dipeptidic products described above are highly stable under several conditions, and are suitable for being admixed with acceptable carriers and compounds conventionally used in dermatological and/or hair care compositions.

The dermatologically (and also pharmacologically) acceptable carrier incorporated in the composition of the present invention may be any carrier conventionally used in the art for the dermatological and/or hair care composition. Examples thereof include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, high-molecular weight compounds, and water-based mixtures and emulsion mixtures of carriers optionally selected from the above-mentioned carriers.

The dermatologic and/or hair care composition of the present invention may further contain various components conventionally used in cosmetics and drugs, etc. Examples of such components include vitamin A such as vitamin oil, retinol and retinol acetate; vitamin $B_2$ such as riboflavin, butyric riboflavin and flavin adenine dinucleotide; vitamin $B_6$ such as pyridoxin hydrochloride and pyridoxin dioctanoate, vitamin C such as L-ascorbic acid, L-ascorbic acid dipalmitic acid ester, L-ascorbic acid-2-sodium sulfate, L-ascorbic acid phosphoric acid ester, DL-α-tocopherol-L-ascorbic acid phosphoric acid diester dipotassium, pantothenic acids such as calcium pantothenate, D-pantothenyl alcohol, panthothenyl ethyl ether and acetylpanthotheyl ethyl ether, vitamin D such as ergocalciferol and cholecalciferol; nicotinic acids such as nicotinic acid, nicotinic acid amide and benzyl nicotinate; vitamin E such as α-tocopherol, tocopherol acetate, DL-α-tocopherol nicotinate and DL-α-tocopherol cinnamate; vitamins such as vitamin P and biotin; oils such as avocado oil, palm oil, peanut oil, beef tallow, rice bran oil, jojoba oil, evening primrose oil, carnauba wax, lanolin, liquid paraffin, squalane, isostearyl palmitate, isostearyl alcohol and glycerol tri-2-ethylhexanoate; humectants such as glycerol, sorbitol, polyethylene glycol, 1,3-butylene glycol, collagen, hyaluronic acid, chondroitin sulfate and sodium dextran sulfate; ultraviolet absorbers such as amyl p-di-methylaminobenzoate, octyl methoxycinnamate, 4-tert-butyl-4-methoxy-dibenzoyl-methane, glyceryl di-p-methoxycinnamate mono-2-ethyl hexanoate, 2-hydroxy-4-methoxybenzophenone, sodium 2-hydroxy-4-methoxybenzophenone-5-sulfonate, urocanic acid and ethyl diisopropylcinnamate; antioxidants such as sodium erythorbate and p-hydroxyanisole; surfactants such as sodium stearylsulfate, diethanolamine cetylsulfate, cetyltrimethylammonium saccharin, polyethylene glycol isostearate, polyoxyethyleneoctyldodecyl alcohol, sorbitan monoisostearate, polyoxyethylenehydrogenated castor oil, glyceryl arachidate, diglycerol diisostearate and phospholipid; preservatives such as methyl p-oxybenzoate, ethyl p-oxybenzoate and butyl p-oxybenzoate; antiphlogistics such as glycyrrhizinic acid derivatives, glycyrrhezinic acid derivatives, salicylic acid derivatives, hinokitiol, zinc oxide and allantoin; beauty whitening agents such as placental extract, glutathione and saxifrage extract; extracts from phellodendron, coptis rhizome, lithospermum, plony root, swertia herb, birch, sage, loquat, carrot, aloe, mallow, iris, grapes, coix seed, dishcloth gourd, lily, saffron, cnidium rhizome, ginger, Saint-John's-wort, ononis, rosemary and garlic, activating agents such as royal jelly, photosensitive principle, cholesterol derivatives and infant bovine blood extract; blood flow quickening agents such as γ-oryzanol; antiseborrheic agents such as sulfur and thianthol; thickeners such as carboxyvinyl polymer, carboxymethyl cellulose and carboxyhydroxypropyl cellulose; perfumes; water; alcohols; coloring materials such as titanium yellow, carthamin and safflower red, and powdery resins such as polyethylene and nylon.

The dosage form of the dermatological and/or hair care composition according to the present invention is not limited. Examples thereof include solubilized preparations such as water or oil preparations, beauty wash, emulsions such as milky lotions and creams, and ointments, dispersions and powders.

Particular dermatological and/or hair care compositions and the constituents thereof are described, but are by no means limited to, the following (the amounts are not limited to those specifically given and are expressed in terms of % by weight):

Cosmetic liquid: Dipeptide component (5.0); tocopherol acetate (0.01); glycerol (4.0); 1,3-butylene glycol (4.0); ethanol (7.0); polyoxyethylene (50 mol) oleyl alcohol ether (0.5); methyl p-oxybenzoate (0.2); citric acid (0.05); sodium citrate (0.1); perfume (0.05) and purified water (balance). Citric acid, sodium citrate, glycerol, 1,3-butylene glycol and dipeptide component are to be dissolved in the purified water. Separately, polyoxyethylene oleyl alcohol ether, tocopherol acetate, perfume and methyl p-oxybenzoate are to be dissolved in ethanol. The resulting solution is to be added to the purified water solution for solubilization, and the mixture is to be filtrated to give a cosmetic liquid.

Cream: (1) Cetostearyl alcohol (3.5); (2) squalane (40.0); (3) beeswax (3.0); (4) reduced lanolin (5.0); (5) ethyl p-oxybenzoate (0.3); (6) polyoxyethylene (20 mol) sorbitan monopalmitate (2.0); (7) monoglyceride stearate (2.0); (8) sodium N-stearoyl glutamate (0.5); (9) 2-hydroxy-4-methoxybenzophenone (1.0); (10) retinol acetate (2.0); (11) evening primrose oil (0.05); (12) perfume (0.03); (13) dipeptide component (0.01); (14) 1,3-butylene glycol (5.0); (15) polyethylene glycol 1500 (5.0) and (16) purified water (balance). The components (1), (2), (3), (4), (5), (6), (7), (8), (9), (10), (11) and (12) are to be heat-dissolved in each other, and the solution is to be added to the components (13), (14), (15) and (16) heated to 75° C. with stirring. The mixture is to be treated by a homomixer to reduce the size of emulsified particles, and rapidly cooled while stirring to give a cream.

Milky lotion: stearic acid (1.5); cetyl alcohol (0.5); beeswax (2.0); polyoxyethylene (10 mol) monooleate (1.0); octyl methoxycinnamate (2.0); magnesium L-ascorbate phosphate (0.2); dipeptide component (1.0); sodium hyaluronate (0.1); triethanolamine (0.75); glycerol (7.0); ethanol (3.0); ethyl p-oxybenzoate (0.3); perfume (0.03) and purified water (balance). The perfume is to be added to ethanol, to dissolve the perfume (alcohol phase). The glycerol, triethanolamine, sodium hyaluronate, DL-α-tocopherol-L-ascorbic acid phosphoric acid diester dipotassium and the dipeptide are to be added and dissolved in the purified water, and the solution is to be maintained at 70° C. (aqueous phase). The other components are to be mixed and heat-dissolved with each other, and the solution is then to be maintained at 70° C. (oil phase). The oil phase is to be added to the aqueous phase to conduct a preliminary emulsification, and the mixture is to be homogeneously emulsified by a homomixer. The emulsion is to be added to the alcohol phase while stirring, and the mixture is to be cooled to 30° C. while stirring to give an emulsified solution.

Foam: (1) Dipeptide component (0.5); (2) 1,3-butylene glycol (5.0); (3) glycerol (7.0); (4) methyl p-oxybenzoate (0.1); (5) potassium hydroxide (0.15); (6) stearic acid (0.5); (7) myristic acid (1.0); (8) batyl alcohol (1.5); (9) polyoxyethylene (60 mol)-hydrogenated castor oil (3.0); (10) perfume (0.05); (11) liquefied petroleum gas (6.0); (12) dimethyl ether (3.0) and (13) purified water (balance). The components (1), (2), (3), (4) and (5) are to be added and heat-dissolved in the component (13) at 70° C., and a solution prepared by heat-dissolving the components (6), (7), (8), (9) and (10) with each other at 75° C. are to be added thereto. The mixture is to be thoroughly stirred and then cooled, and thereafter, the mixture is to be packed into a vessel, and the components (11) and (12) are to be finally packed into the vessel to give a foam mask.

Ointment: Dipeptide component (0.5); tocopherol acetate (1.0); retinol palmitate (0.5); stearyl alcohol (18.0); Japan wax (20.0); polyoxyethylene (20 mol) monooleate (0.25); glycerol monostearate (0.3); petrolatum (40.0) and purified water (balance). The dipeptide component is to be added to the purified water, and the solution is to be maintained at 70° C. (aqueous phase). The remaining components are to be mixed and dissolved in each other at 70° C. (oil phase). The oil phase is to be added to the aqueous phase, and the mixture is to be homogeneously emulsified by a homomixer and then cooled to give an ointment.

Aspects (2) of the invention pertains to a cosmetic method comprising topically applying the dermatological and/or hair care composition as of aspect (1) as defined hereinbefore to the human or animal skin and/or hair. In a preferred embodiment the method is for vitalizing or anti-aging treatment of the human skin, or for vitalizing, conditioning, or against hair loss of the human or animal hair. Although the amount applied of the dermatological composition according to the present invention is not particularly limited, it is preferred that the composition is applied twice a day in an amount of 1.5 to 2 ml each time for the beauty wash, 1 to 1.5 ml each time for the milky lotion, and about 0.2 g each time for the cream.

Aspect (3) of the invention pertains to the use of the dermatological and/or hair care composition of aspect (1) as defined hereinbefore for vitalizing or in an anti-aging treatment of the human or animal skin, and/or for vitalizing, conditioning, or against hair loss of the human or animal hair. For preferred embodiments of aspect (3), those of aspect (2) equally apply.

The DIP1 CGPase CphE$_{al}$ was deposited by Westfalische Wilhelms-Universitat Munster, Corrensstr. 3, 48149 Münster, Germany with the DSMZ-Deutsche Sammlung von Mikroorganismen and Zellkulturen GmbH, Inhoffenstr. 7b, 38124 Braunschweig, Germany as DSM 21533.

The invention will be further described in the following Examples, which are not to be construed as limiting the invention.

EXAMPLES

Materials and Methods (In Vitro Studies; Examples 1 and 2):

Production of dipeptide compositions: CGP and the extracellular CGPase enzyme were produced via separate fermentations before the final CGPase-catalysed breakdown of CGP into dipeptides took place. A recombinant strain of *Ralstonia eutropha* H16-PHB⁻4-Δeda (pBBR1MCS-2::cphA$_{6308}$/edaH16) was used for the production of CGP in a 500L fermentation, while the CGPase was produced with *P. alcaligenes* strain DIP1 CphE$_{al}$ having been deposited with the DSMZ as DSM 21533. CGP was then extracted from the produced biomass and purified. CGPase enzyme was purified from the culture supernatant. The produced CGP and the CGPase were then combined under specific conditions, upon which the biopolymer was broken down into its constituent β-dipeptides. The β-L-aspartyl-L-arginine and β-L-aspartyl-L-lysine dipeptide fractions were then separated from the remainder of the reaction, analyzed for purity via HPLC, and finally dried to a powder (WO2009150252 and Sallam et al., AEM 75:29-38(2009)). The pure β-dipeptides were utilized in the following experiments.

Experimental application of test-products: In this study 30 μl of a 5% aqueous solution of the test substances were applied as follows using a calibrated pipette:

Vitality/viability testing (Example 1): once a day (see Tab. 1) topically as well as systemically, with sterile water (negative) and Triton® X-100 (positive) as controls, and analysis time points at 48 and 120 h.

Proliferation testing of basal Keratinocytes (Example 2): topically with air exposed models as reference and analysis time points for proliferation rate after 3 and 6 days.

Application was done in duplicates (2 models) at all time points and models were cultured and analyzed in parallel under identical conditions.

EpiDerm 3D-Epidermal skin models: Nowadays in vitro test procedures are a very good alternative to animal experiments and become increasingly important for the cosmetic industry. For cosmetic products which are used over a longer period, dermatological tests for harmlessness are an essential prerequisite for a high application safety and customer satisfaction. During the development of new cosmetic products biological effects of particular active ingredients or complete formulations turn into focus of cosmetic interests.

The human EpiDerm skin model is an in vitro reconstructed multilayered epithelial tissue which is cultured of normal human keratinocytes. Compared to the explant of natural human skin the model shows all typical layers (stratum basale-, spinosum-, granulosum-, and stratum corneum) of native human skin. The model is mitotically as well as metabolically active and expresses typical differentiation marker like pro-fillagrin 1 and cytokeratin 1/10. Moreover, the model shows many characteristics of the human skin barrier whereby it is well suited for cosmetic application studies and in vitro analyses (P. Hayden et al., GTAM 2011, Newark, USA (2011)). The utilized 3D-Epidermis skin models were purchased from MatTek Corporation, Ashland, USA and cultured under optimal atmospheric conditions with 37° C., 95% $H_2O$ and 5% $CO_2$ following manufactures instructions.

MTT-Assay for the in-Vitro Epidermal Vitality/Viability Testing (Example 1): Viability is considered as the comprehensive capacity of life. This term summarizes all metabolic activities which cells need for their basic requirements as well as for growth and proliferation. An established method to measure vitality of cells and tissues is the MTT-Vitality-Assay. 3-(4,5-Dimethylthiazol-yl)-2,5-diphenyl-tetrazoli-umbromide, briefly called MTT, is a yellow, water-soluble salt which is turned into a purple-blue formazan inside the cells, through a chemical reduction of the tetrazolium ring (T. Weiss et al., Toxicol. In Vitro J. 18(3):231-43 (2004); M. V. Berridge et al., Biochemica 4:14-19 (1996)). The formazan crystals precipitate into the cellular cytosol, whereby the amount of precipitate correlates quantitatively with the general cellular vitality. Therefore the MTT-Assay can be considered as an indicator for the vitality or "Fitness" of a tissue, because cellular processes like respiration and energy extraction lead to the reduction of MTT.

Aim of this experiment was to examine the potential of the test substances to vitalize the tissue. For this purpose 3D-Epidermis skin models were used. The utilized skin models were incubated in assay medium (MatTek) with 1 mg/ml MTT-Solution for 3 h at 37° C., 95% $H_2O$, 5% $CO_2$ in the dark. After incubation period the bottom of model jars were dabbed with a sterile wipe to remove excessive medium/MTT mix. Models were transferred to a new sterile 24 well plate and 2 ml isopropyl was added subsequently. To avoid evaporation, plates were sealed with parafilm, covered with tinfoil and incubated 2 h on a shaker to extract formazan crystals. Optical density of released crystals of all extracts was determined at 570 nm. Measured values were analyzed and assessed. The $OD_{570}$ of the negative control (water) had to be minimal 0.8. The variation coefficient (CV) of identical treated samples has to be <30% with the exception of samples below 0.3. The vitality was derived from averages of determined ODs whereby the water treated, optimal cultured control was set as 100% vitality [vitality: $100*(OD_{test\ substance}/OD_{control})$].

TABLE 1

Study design and implementation

Experimental setup of the study
topical and systemical application of test substances via a calibrated pipette

| | Incubation period [h]/amount of used models | |
|---|---|---|
| test substance 30 μl each | 48 h | 120 h |
| sterile water | 2 | 2 |
| β-L-aspartyl-L-lysine | 2 (2) | 2 (2) |
| β-L-aspartyl-L-arginine | 2 (2) | 2 (2) |

TABLE 1-continued

Study design and implementation

Experimental setup of the study
topical and systemical application of test substances via a calibrated pipette

| | Incubation period [h]/amount of used models | |
|---|---|---|
| test substance 30 μl each | 48 h | 120 h |
| 1% Triton ® X-100 | 2 | 2 |
| End point | | MTT-Vitality-Assay |
| Finalizing | | Evaluation & assessment |

Evaluation of the proliferation rate of basal keratinocytes (Example 2): The human skin composes of epidermis, dermis and subcutis. The epidermis rests on the papillary dermis and is anchored through a basal lamina consistent of extracellular matrix proteins, which is called the dermo-epidermal junction zone (F. Chehrehasa et al., J. Neu Meth. 177:122-130 (2009); A. Tuschil et. al., J. Invest. Dermatol. 99:294-298 (1992)). The epidermis possesses a basal cell layer with constantly growing cells (basal keratinocytes). and the percentage of proliferating nuclei (red fluorescence) was determined.

Fluorescence microscopy: Click-iT®-EdU tagged cells were stained in red (λex 594 nm). The entire nuclei of the tissue were counterstained in blue with DAPI (λex 358 nm). Click-iT®-EdU and DAPI stained cells were recorded solely and merged subsequently. The fluorescence analysis and documentation was performed with the ZEISS, Axio Scope A1HAL 100.

TABLE 2

Study design and implementation

Experimental setup of the study
topical application of test substances via a calibrated pipette

| | Incubation period [d]/amount of used models | |
|---|---|---|
| test substance 30 μl each | 3 d | 6 d |
| air exposed | 2 | 2 |
| β-L-aspartyl-L-lysine | 2 | 2 |
| β-L-aspartyl-L-arginine | 2 | 2 |
| End point | | proliferation rate of basal keratinocytes |
| Finalizing | | Evaluation & assessment |

Those cells act exclusively for the epidermal regeneration and the retention of tissue homeostasis. New born cells arise though the process of mitosis and migrate into suprabasal layers (stratum spinosum) where they lose the ability to proliferate and start to differentiate. At the end of this process highly differentiated cells from the stratum granulosum cornify, die and constitute the stratum corneum. The origination of keratinocytes within the basal layer compensates the loss of cells which desquamate from the horny layer. This leads to a constantly and uniformly renewal of epidermal cells and the maintenance of epidermal homeostasis (H. J. Stark et al., J. Inv. Derm. 11:93-105 (2006); H. A. Rennekampff et. al., J. Surg.l Res. 93:41-54 (2000)).

Click iT®-EdU (cell proliferation assay): To specifically tag growing and proliferating basal keratinocytes the Click-iT®-EdU-Assay (Life Technologies) was utilized (F. Chehrehasa et al., J. Neu Meth. 177:122-130 (2009)). 5-Ethylnyl-2'-Deoxyuridine (EdU) is a thymidine base analog which terminal methyl group was exchanged with an ethyne group. This ethyne group reacts with a fluorescent active azide and enables a visual molecular detection of replicating DNS within the synthesis-phase (S-phase) of mitosis.

Evaluation of the proliferation rate: Out of every used skin model, 6 mm punch biopsies were taken, embedded in O.C.T.™, cryoconserved in the gaseous phase of liquid nitrogen and subsequently cut into 5-6 μm sections. Nuclei from every section were counted (blue fluorescence, DAPI)

Materials and Methods (In Vivo Trials; Example 3):

Production of dipeptide compositions: both dipeptides were produced and analyzed according to the procedures described for the in vitro tests above.

Panelists: The test panel included 5 adult female volunteers with dry skin, elasticity less than average and crow's feet wrinkles next to the eyes. At the beginning of the application test all subjects have been checked by a dermatologist. Only subjects were allowed to join the trial with no pathological skin modifications diagnosed. During the application test all subjects had in case of acute skin irritations access to daily consultations from an attending medical specialist who was accompanying the test. Daily consultations about the skin conditions through the test-accompanying medical doctor were possible.

Experimental application of test-products: Test areas were around 3 cm in diameter. The test products were applied on the volar forearm (5% and 10% aqueous solutions; skin elasticity and hydration tests) as well as the crows's feet wrinkles (5% aqueous solution). The application of the preparations have been done twice a day during the whole test period (4 weeks). The subjects have been instructed not to use other care products in this test area. Untreated skin areas were used as control.

Elasticity test: The test was performed with the cutometer MPA 580 Fa. Courage+Khazaka electronics GmbH. The principle of measurement is based on the suction/elongation principle. To obtain start conditions the instrument was adjusted for 450 mbar low pressure. The suction time was defined to 5 secs. The relaxation time (abrupt loss of low pressure) was fixed to 3 secs. All measurements have been repeated three times for each test and control areas. Afterwards a mean for R2-values obtained from three independent measurements per area has been calculated. To perform measurements the instrument was adjusted for the named parameters before the test was started. All parameter adjustments described in literature as mainly used and reliable remained unchanged during the measurements. The cutometry has been performed at the beginning and at the end of the application period. R2-values have been measured and analyzed for each subject.

Skin moisture: this aspect was tested using the Corneometer CM 825 (Firma Courage+Khazaka). The test products were applied twice a day on the relevant pre-determined skin areas during the application period. The test persons were acclimatized for 45 minutes at a temperature of 22 degrees centigrade and 60% relative humidity before every measurement, then, the skin measurement values were measured at three different places within the respective testing areas. The recorded values were averaged. Untreated skin close to the test area was used as the control measurement area. Measurements were taken before the application and after four weeks of application. All measurements were performed at least 10-12 hours after the last application of the formerly used product resp. the test product.

Single wrinkles depth: Optical 3D measurement using a PRIMOS (Phaseshift Rapid In vivo Measurement Of Skin) compact portable system was used for this measurement. PRIMOS comact portable was applied on an area of 40×30 mm and digital fotos of the measured area were made. A lateral resolution of 63 μm and a depth resolution of ≥4 μm were applied to measure the 3D-pictures (measuring accuracy is ≥5 μm). For a particular density of points selected for the x and y axes, a computer program draws a realistic three-dimensional image of the relief of the skin on a colour screen. Finally, the measurement data generated were processed and then evaluated. This analysis consists of the following stages: 1. Matching procedure of reference area and skin surface to be compared with 2. Measuring of geometric data e.g. depth, distance, or radius. With the PRIMOS software the changes in structure of the epidermis can be classified quantitatively with the aid of various standardized surface measurement parameters in accordance with DIN (Deutsche Industrie Norm, German industrial standards) and ISO (International Standards Organisation). The calculations are carried out by reference to the relevant DIN-standards, and long-wave profile elements are removed as required by polynomials. The profile of the cut view used here serves to provide the depth of a single wrinkle. The skinfold depth can be measured by determining the distances.

Example 1

In-Vitro Epidermal Vitality/Viability

As shown in FIG. 1 all utilized test substances led to an increased vitality after 48 h of incubation, compared to water treated models. The positive control, 1% Triton® X-100, decreased the cell vitality below 50% (7.12%) as expected. The highest value (127.23%) after 48 hours of systematical incubation was objectified for the dipeptide β-L-aspartyl-L-arginine.

The topical application of test substances resulted in elevated tissue vitalities as well (see FIG. 2), but not to that distinct extent as for the systematical application. This was most likely the case due to the better bioavailability of the test products systematically applied, because they didn't have to pass the skin barrier. Highest values (112.36%) were again observed for the substance β-L-aspartyl-L-arginine.

After 120 h systemically incubation slightly lower values (see FIG. 3) were objectified, compared to 48 h. Highest values (118.16%) were observed again for the test substance β-L-aspartyl-L-arginine.

After 120 h of topical application higher values were observed, compared to 48 h results (see FIG. 4). Due to the longer incubation time a sufficient concentration of test substances seemed to reach deeper cell layers and got available for the cells. Highest values (120.61%) were observed also here for the test dipeptide β-L-aspartyl-L-arginine.

The present vitality test revealed that the tested substances were very well tolerated by the utilized 3D-Epidermal skin models. Every substance showed a vitalizing effect on skin cells after 48 h and 120 h regardless of application mode. Short term application (48 h) showed slightly higher vitality rates through systemically application whereas after long term incubation (120 h) the topical applied models had higher vitality rates. The highest values were consistently observed with the dipeptide β-L-aspartyl-L-arginine.

Example 2

In-Vitro Proliferation of Basal Keratinocytes

Air exposed skin models were compared with substances-treated ones regarding the proliferation rate of epidermal basal keratinocytes. Models were cryoconserved, histologically prepared and specifically stained after respective incubation period (e.g. FIG. 5 after 3 days). To assess the proliferation rate, basal keratinocytes were counted and the relation between red fluorescing (proliferative) and blue fluorescing (not proliferative) was determined (see FIG. 5). A minimum of 1500 nuclei were counted for every test substance and for the air exposed models, twice. The counting results were summarized in Tables 3 and 4.

TABLE 3

Summarized counting of proliferative cells after 3 days incubation

| test substance | nuclei counted | proliferative | percentage |
|---|---|---|---|
| air exposed | 2176 | 244 | 11.21 |
| β-L-Aspartyl-L-Lysine | 2591 | 423 | 16.33 |
| β-L-Aspartyl-L-Arginine | 1785 | 553 | 30.98 |

After 3 days incubation period it was found that the dipeptide β-L-aspartyl-L-lysine (16.33%) increased the proliferation activity of basal keratinocytes, compared to air exposed models (11.21%), while the highest ratio was found in models treated with the dipeptide β-L-aspartyl-L-arginine with 30.98%.

TABLE 4

Summarized counting of proliferative cells after 6 days incubation

| test substance | nuclei counted | proliferative | percentage |
|---|---|---|---|
| air exposed | 1876 | 321 | 17.11 |
| β-L-aspartyl-L-lysine | 2133 | 472 | 22.12 |
| β-L-aspartyl-L-arginine | 2047 | 656 | 32.05 |

After 6 days the dipeptide β-L-aspartyl-L-arginine showed the highest determined proliferation increase confirming the results obtained after 3 days.

The present study revealed that the tested substances were very well tolerated by the utilized 3D-Epidermal skin models. No negative effect on tissue vitality or morphology was observed.

Every substance showed a stimulating effect on basal keratinocyte proliferation of 3D-skin models which was most prominent for the dipeptide β-L-aspartyl-L-arginine.

Example 3

In-Vivo Trials for Skin Tolerability, Elasticity, Hydration, and Single Wrinkle Depth Tolerability: All of the 5 study participants tolerated both test products and all tested concentrations very well during the course of the four-week application test under dermatological and clinical criteria. There were no undesired or pathological skin reactions in the test area.

Skin elasticity: β-L-aspartyl-L-arginine: In the treated area volar forearm, an improvement in skin elasticity of about 9.11% for the 5% aqueous solution and 8.70% for the 10% aqueous solution was measured. The average improvement in the skin elasticity on the forearm after 4 weeks of product application amounted to 9.26% (5% aqueous solution) and 8.85% (10% aqueous solution) as well as 8.08% improvement in the crow's feet area (5% aqueous solution) after control area deduction.

β-L-aspartyl-L-lysine (5%): In the treated area volar forearm, an improvement in skin elasticity of about 6.03% was measured. In the treated area crow's feet (left eye) an average improvement of 11.06% was measured. The average change in skin elasticity in the untreated control area amounted to −0.15%. The average improvement in the skin elasticity on the forearm after 4 weeks of product application amounted to 6.18% as well as 11.21% improvement in the crow's feet area after control area deduction.

Skin hydration: β-L-aspartyl-L-arginine: In the treated area volar forearm, an improvement in skin moisture of about 1.126% (5% aqueous solution) and 0.871% (10% aqueous solution) was measured. In the treated area crow's feet (next to the eye) an improvement of skin moisture about 1.873% was measured. The average change in skin moisture in the untreated control area amounted to 0.31%. The average improvement in the skin moisture after 4 weeks of product application amounted to 0.82% and 0.56% at the volar forearm and 1.56% at the crow's feet (after control area deduction).

β-L-aspartyl-L-lysine (5%): In the treated area volar forearm, an improvement in skin moisture of about 2.05% was measured. In the treated area crow's feet (next to the eye) an improvement of skin moisture about 16.10% was measured. The average change in skin moisture in the untreated control area amounted to 0.31%. The average improvement in the skin moisture after 4 weeks of product application amounted to 1.74% at the volar forearm and 15.79% next to the eyes (after control area deduction).

Single wrinkle depth: The wrinkle depth of one single wrinkle has been measured on 5 subjects before and after using the preparations for a period of four weeks to determine the effect of the preparation 5% aqueous solutions of the test products.

The skin wrinkles were measured using the extended optical 3D-measurements of the surface of the skin. In the treated areas, the average improvement in the wrinkle depth amounted to 16.4% in case of β-L-aspartyl-L-arginine, and to 20.02% in case of β-L-aspartyl-L-lysine (see FIG. 6).

The invention claimed is:

1. A cosmetic method comprising topically applying a composition comprising one or more β-dipeptides, or oligomers thereof, or salts thereof, wherein each of the β-dipeptides comprises βL-aspartyl as a first amino acid residue, to the human or animal skin or hair, wherein the composition increases the vitality of skin cells and/or the proliferation activity of basal keratinocytes in the human or animal skin or hair.

2. The method of claim 1, wherein the composition comprises dipeptides selected from the group consisting of β-L-aspartyl-L-arginine, β-L-aspartyl-L-lysine, and a mixture of β-L-aspartyl-L-arginine and β-L-aspartyl-L-lysine.

3. The method of claim 1, which is for vitalizing, moisturizing, anti-aging, skin conditioning, hair conditioning or hair growth stimulating.

4. The method of claim 1, wherein a second amino acid residue is selected from arginine, lysine, ornithine, glutamate, citrulline, and canavanine.

5. The method of claim 4, wherein the second amino acid residue is of L- or D-configuration.

6. The method of claim 1 wherein the oligomer comprises two or more covalently bound β-dipeptides.

7. The method of claim 1, wherein one or more of the β-dipeptides are chemically modified.

8. The method of claim 1, wherein the composition comprises from 0.00001 to 50 wt. % of β-dipeptides or oligomers thereof.

9. The method of claim 1, wherein the composition further comprises one or more free amino acids or salts thereof.

10. The method of claim 9, wherein the composition comprises from 0.001 to 10 wt. % of free amino acids.

11. The method of claim 1, wherein the composition further comprises a supportive component selected from the group consisting of vitamins, fatty acids, minerals or trace elements conventionally used in dermatological and/or hair care compositions including vitamin A, C, D, E, B5, B6, B7, B12, folic acid, omega-3, selenium, zinc, magnesium, and iron.

12. The method of claim 1, wherein the composition further comprises a dermatologically and/or hair care acceptable carrier, selected from the group consisting of water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, high-molecular weight compounds, and water-based mixtures and emulsion mixtures of the above-mentioned carriers, and components conventionally used in dermatological and/or hair care compositions.

13. The method of claim 1, wherein the composition is an external/topically applicable dermatological and/or hair care composition.

14. The method of claim 1, wherein the composition consists of (i) one or more β-dipeptides, or oligomers thereof, or salts thereof and (ii) at least one dermatologically and/or hair care acceptable carrier.

* * * * *